(12) United States Patent
Genkin et al.

(10) Patent No.: US 9,072,733 B2
(45) Date of Patent: *Jul. 7, 2015

(54) METHOD FOR TREATING SYSTEMIC BACTERIAL, FUNGAL AND PROTOZOAN INFECTION

(71) Applicant: CLS Therapeutics Limited, St Peter Port, Guernsey, Channel Island (GB)

(72) Inventors: Dmitry Dmitrievich Genkin, Saint-Petersburg (RU); Georgy Viktorovich Tets, Saint-Petersburg (RU); Viktor Veniaminovich Tets, Saint-Petersburg (RU)

(73) Assignee: CLS THERAPEUTICS LIMITED (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/787,533

(22) Filed: Mar. 6, 2013

(65) Prior Publication Data

US 2013/0183284 A1    Jul. 18, 2013

Related U.S. Application Data

(63) Continuation of application No. 12/835,036, filed on Jul. 13, 2010, now Pat. No. 8,431,123, which is a continuation-in-part of application No. 10/564,609, filed as application No. PCT/RU2004/000260 on Jul. 1, 2004, now abandoned.

(30) Foreign Application Priority Data

Jul. 14, 2003    (WO) ............... PCT/RU2003/000304
Mar. 12, 2004    (RU) ............................... 2004108057

(51) Int. Cl.
A61K 38/46    (2006.01)

(52) U.S. Cl.
CPC ............... *A61K 38/465* (2013.01); *A61K 38/46* (2013.01)

(58) Field of Classification Search
CPC ............................ A61K 38/46; A61K 38/465
USPC ............. 435/196, 16, 6.1; 530/350; 536/23.2; 424/94.6
See application file for complete search history.

(56) References Cited

U.S. PATENT DOCUMENTS

| | | | |
|---|---|---|---|
| 4,485,095 A | 11/1984 | Fujisaki et al. | |
| 5,484,589 A | 1/1996 | Salganik | |
| 5,656,589 A | 8/1997 | Stossel et al. | |
| 5,889,153 A | 3/1999 | Suzuki et al. | |
| 5,952,170 A | 9/1999 | Stroun et al. | |
| 6,033,846 A | 3/2000 | Fournie | |
| 6,156,504 A | 12/2000 | Gocke et al. | |
| 6,391,607 B1 | 5/2002 | Lazarus et al. | |
| 6,428,785 B1 | 8/2002 | Gokeen | |
| 6,455,250 B1 | 9/2002 | Aguilera et al. | |
| 6,465,177 B1 | 10/2002 | Hoon | |
| 6,521,409 B1 | 2/2003 | Gocke et al. | |
| 7,612,032 B2 | 11/2009 | Genkin et al. | |
| 2003/0044403 A1 | 3/2003 | Shak | |
| 2004/0001817 A1 | 1/2004 | Giampapa | |
| 2004/0157239 A1 | 8/2004 | Tanuma et al. | |
| 2006/0228347 A1 | 10/2006 | Sunaga et al. | |
| 2006/0233780 A1 | 10/2006 | Genkin et al. | |
| 2008/0004561 A1 | 1/2008 | Genkin et al. | |
| 2009/0047272 A1 | 2/2009 | Appelbaum et al. | |
| 2009/0053200 A1 | 2/2009 | Genkin et al. | |
| 2010/0061971 A1 | 3/2010 | Genkin et al. | |
| 2010/0150903 A1 | 6/2010 | Genkin et al. | |
| 2010/0303796 A1 | 12/2010 | Genkin et al. | |
| 2011/0033438 A1 | 2/2011 | Bartoov et al. | |
| 2011/0070201 A1 | 3/2011 | Shaaltiel et al. | |

FOREIGN PATENT DOCUMENTS

| | | |
|---|---|---|
| CA | 2394856 | 6/2001 |
| CA | 2184582 | 12/2001 |
| DE | 4024530 | 2/1992 |
| DE | 10221194 | 12/2003 |
| EP | 0325191 | 7/1989 |
| EP | 1666055 | 2/2005 |
| EP | 1655036 | 5/2006 |
| EP | 1880733 | 1/2008 |
| EP | 2095825 | 6/2011 |
| GB | 984464 | 2/1965 |
| GB | 1005985 | 9/1965 |
| JP | 61293927 | 12/1986 |
| JP | 2006-290769 | 10/2006 |

(Continued)

OTHER PUBLICATIONS

Department of Health and Human Services Food and Drug Administration, Federal Register, vol. 50, No. 240, Friday, Dec. 13, 1985, Part II, excerpt from p. 51104.
Lee, D., Continued marketing of a useless drug ('Varidase') in Panama, Lancet, vol. 335, p. 667, 1990.
Roche, Pulmozyme®, Dornase alfa solution for inhalation 1.0 mg/ml, Data Sheet, 2008.
Varidase Buccal Tablets product information from Lederle Laboratories Inc., Canad. M. A. J., vol. 84, pp. 867-868, 1961.
Anker, P. et al., Tumor-related alterations in circulating DNA, potential for diagnosis, prognosis and detection of minimal residual disease, Leukemia, 15, 289-91, 2001.

(Continued)

*Primary Examiner* — Delia Ramirez
(74) *Attorney, Agent, or Firm* — Troutman Sanders LLP

(57) ABSTRACT

The invention is directed to a treatment of systemic bacterial, fungal and protozoan infections. The inventive method comprises introducing a DNase enzyme into a circulating blood system of a patient diagnosed with systemic infection caused by bacteria, fungi or protozoa, wherein said DNase enzyme destroys extracellular DNA in said blood of said patient, said DNase enzyme being administered in doses and regimens which are sufficient to decrease the average molecular weight of circulating extracellular blood DNA in the blood of said patient.

2 Claims, 3 Drawing Sheets

(56) References Cited

FOREIGN PATENT DOCUMENTS

| | | |
|---|---|---|
| NZ | 299257 | 8/2000 |
| RU | 2099080 | 12/1997 |
| RU | 2001104426 | 1/2003 |
| RU | 2202109 | 4/2003 |
| RU | 2207876 | 7/2003 |
| RU | 2239404 | 11/2004 |
| RU | 2239442 | 11/2004 |
| RU | 2267329 | 1/2006 |
| RU | 2269356 | 2/2006 |
| RU | 2269357 | 2/2006 |
| RU | 2269359 | 2/2006 |
| RU | 2308968 | 10/2007 |
| WO | WO93/03709 | 3/1993 |
| WO | WO95/00170 | 1/1995 |
| WO | WO97/28266 | 8/1997 |
| WO | WO97/47751 | 12/1997 |
| WO | WO00/03709 | 1/2000 |
| WO | WO00/31238 | 6/2000 |
| WO | WO01/74905 | 10/2001 |
| WO | WO03/068254 | 8/2003 |
| WO | WO2005/004903 | 1/2005 |
| WO | WO2005/004904 | 1/2005 |
| WO | WO2005/007187 | 1/2005 |
| WO | WO2005/115444 | 12/2005 |
| WO | WO2006/130034 | 12/2006 |
| WO | WO2008/047364 | 4/2008 |
| WO | WO2008/066403 | 6/2008 |
| WO | WO2011/073665 | 6/2011 |
| WO | WO2012/075506 | 6/2012 |

OTHER PUBLICATIONS

Ashton, G., Growing pains for biopharmaceuticals, Nature Biotech, vol. 19, pp. 307-311, 2001.
Aung et al., Current status and future potential of somatic mutation testing from circulating free DNA in patients with solid tumours, Hugo J, vol. 4, pp. 11-21, 2010.
Botto, N., et al., Elevated levels of oxidative DNA damage in patients with coronary artery disease, Coronary Artery Disease, vol. 13, pp. 269-274, 2002.
Boyko et al., Cell-free DNA—a marker to predict ischemic brain damage in a rat stroke experimental model, Journal of Neurosurgical Anesthesiology, vol. 23, pp. 222-228, 2011.
Burt et al., Detection of circulating donor deoxyribonucleic acid by microsatellite analysis in a liver transplant recipient. Liver Transpl Surg. (2), pp. 391-394, 1996.
Davis JC et al., Recombinant human Dnase I (rhDNase) in patients with lupus nephritis, LUPUS, vol. 8, pp. 68-76, 1999.
Dayan, Pharmacological-Toxicological (Expert Report on Recombinant Human Deoxyribonuclease I (rhDNase; PulmozymeTM) , Hum. Exp. Toxicol., 13: S2, 1994.
Deitsch, et al., Transformation of malaria parasites by the spontaneous uptake and expression of DNA from human erythrocytes, Nucleic Acids Research, vol. 29, pp. 850-853, 2000.
Deocharan B., et al., Alpha-actinin is a cross-reactive renal target for pathogenic anti-DNA antibodies, J. Immunol., vol. 168, pp. 3072-3078, 2002.
Department of Health and Human Services Food and Drug Administration, Federal Register, Dec. 13, 1985, vol. 50, No. 240.
Dittmar, Manuela et al., A novel mutation in the *DNASE1* gene is related with protein instability and decreased enzyme activity in thyroid autoimmunity, Journal of Autoimmunity, vol. 32, pp. 7-13, 2009.
El Hassan No, et al. Rescue use of Dnase in critical lung atelectasis mucus retention in premature neonates, Pediatrics., vol. 108, pp. 468-470, 2001.
Extended European Search Report for European Patent Appl. No. EP12170750 dated Aug. 3, 2012.
Extended European Search Report for European Patent Appl. No. EP12170754 dated Aug. 3, 2012.
Extended European Search Report for European Patent Appl. No. EP12170757 dated Aug. 3, 2012.

Favorov, P.V. Issledovaniye kinetiki prevrashchenii DNK pod deistviem DNK-topoizomeraz i DNK-abzimov, author's abstract of PhD thesis in biological sciences, M., pp. 3-4, 1999 (Reference in Russian and English-language translation).
Finlay B., The global diversity of protozoa and other small species, International Journal of Parasitology, vol. 28, pp. 29-48, 1998.
Freshney, R. I., Culture of Animal Cells, A Manual of Basic Technique, Alan R. Liss, Inc., New York, pp. 3-4, 1983.
Funakoshi, A, et al., Clinical Investigation of Serum Deoxyribonuclease: II. Clinical Studies of Serum Deoxyribonuclease Activity in Pancreatic Disease, Gastroenterologia Japonica, vol. 14, pp. 436-440, 1979.
Gal S. and Wainscoat JS, Detection and Quantitation of Circulating *Plasmodium falciparum* DNA by Polymerase Chain Reaction, Methods in Molecular Biology, vol. 336, pp. 155-162, 2006.
Gannushikina, I.V., et al., Plasma DNA Levels in Patients with Atherosclerotic Involvement of the Major Arteries of the Head and lateral Amyotrophic Sclerosis, Bulletin of Experimental Biology and Medicine, vol. 124, No. 12, pp. 1164-1166, 1997 (Translated from: Gannushkina I.V. et al., Uroven DNK v plazme krovi bolnykh s 1-4 ateroskloroticheskim porazheniem magistralnykh artery golovy i bokovym amiotroficheskim sklerozom Byulleten' Experimental'noi Biologii i Meditsiny, Moscow, Meditsina, No. 12, pp. 610-612, 1997).
Gibbs et al., Mechanism-Based Target Identification and Drug Discovery in Cancer Research Science, vol. 287, pp. 1969-1973, 2000.
Gibson et al., Pathophysiology and management of pulmonary infections in cystic fibrosis., Am J Respir Crit Care Med, vol. 168, pp. 918-951, 2003.
Gluhov BM, Znachenije nukleaz v patogeneze neirovirusnyh zabolevanij, Avtoreferat dissertatsii na soiskanie uchenoi stepeni doktora medicinskikh nauk (author's abstract of MD thesis in medical sciences), Novosibirsk, pp. 15-16, 21-26, 1996 (Reference in Russian and English-language translation of pp. 14-17 and 20-27).
Gormally et al., Circulating free DNA in plasma or serum as biomarker of carcinogenesis: Practical aspects and biological significance, Mutation Research, vol. 635, pp. 105-117, 2007.
Gorrini, C., et al., Effect of apoptogenic stimuli on colon carcinoma cell lines with a different c-myc expression level, Int J Mol Med, vol. 11, pp. 737-742, 2003.
Gura, T., Systems for Identifying New Drugs Are Often Faulty, Science, vol. 278, pp. 1041-1042, 1997.
Hann, et al. Building 'validated' mouse models of human cancer. Curr Opin Cell Biol, 13(6), pp. 778-784, 2001.
Horlitz, Martin et al., Optimized Quantification of Fragmented, Free Circulating DNA in Human Blood Plasma Using a Calibrated Duplex Real-Time PCR, PLoS ONE, vol. 4, Issue 9, e7207, 2009.
Huttunen, R., et al., Fatal Outcome in Bacteremia is Characterized by High Plasma Cell Free DNA Concentration and Apoptotoc DNA Fragmentation: A Prospective Cohort Study, PLoS ONE, vol. 6, e21700, 2011.
International Search Report for PCT/RU2003/000304, mailed on Mar. 25, 2004.
International Search Report for PCT/RU2004/000260, mailed on Dec. 9, 2004.
International Search Report for PCT/RU2004/000261, mailed on Oct. 21, 2004.
International Search Report for PCT/RU2004/000262, mailed on Oct. 21, 2004.
International Search Report for PCT/RU2005/000236, mailed on Nov. 24, 2005.
International Search Report for PCT/RU2006/000642, mailed on Aug. 2, 2007.
Juncosa, Barbara, DNA on the Loose: Next-Gen Blood Tests Tap Free-Floating Genetic Material, Scientific American, Mar. 18, 2009.
Jylhava et al., Aging is associated with quantitative and qualitative changes in circulating cell-free DNA: The Vitality 90+ study, Mechanisms of Ageing and Development, vol. 132, pp. 20-26, 2011.
Kalandarishvili F., Nakoplenie spontanno povrezhdennoj DNK v nei postgepatjektomirovannoj pecheni u staryh krys, Med. Novosti Gruzii, No. 5, pp. 11-12, 1998 (Reference in Russian and English-language translation).

(56) References Cited

OTHER PUBLICATIONS

Kaprin et al., Prognoz i lechenie bol'nih poverhnostnim rakom mochevogo puziria visokoi stepeni riska, Visokie Tehnologii v Onkologii, Rostov-na-Donu, vol. 3, pp. 149-150, 2000 (reference in Russian and English-language translation).
Kawane, K, et al., DNAse II deficiency causes chronic polyarthritis in mice, Nature Clinical Practice Rheumatology, vol. 3, No. 4, p. 192, 2007.
Krapf F. et al., The estimation of circulating immune complexes, C3d, and anti-ds-DNA-antibody serum levels in the monitoring of therapeutic plasmapheresis in a patient with systemic lupus erythematosus. A case report, Clin Exp Rheumatol., vol. 3, pp. 159-162, 1985.
Lachmann PJ, Lupus and Desoxyribonuclease, Lupus, vol. 12, pp. 202-206, 2003.
Lecompte, et al., Detection of free-circulating tumor-associated DNA in plasma of colorectal cancer patients and its association with prognosis, Int. J. Cancer, vol. 100, pp. 542-548, 2002.
Lee, D., Continued Marketing of a Useless Drug ('Varidase') in Panama, Lancet, March, vol. 335, p. 667, 1990.
Leland et al., Cancer chemotherapy—ribonucleases to the rescue, Chem. & Bio., vol. 8, pp. 405-413, 2001.
Leon et al., Free DNA in the Serum of Cancer Patients and the Effect of Therapy, Cancer Research, vol. 37, pp. 646-650, 1977.
Li et al., The *Haemophilus ducreyi* cytolethal distending toxin activates sensors of DNA damage and repair complexes in proliferating and non-proliferating cells, Cellular Microbiology, vol. 4, pp. 87-99, 2002.
Liggett et al. , Methylation patterns of cell-free plasma DNA in relapsing-remitting multiple sclerosis, Journal of Neurological Sciences, vol. 290, pp. 16-21, 2010.
Macanovic et al., The treatment of systemic lupus erythematosus (SLE) in NZB/W F1 hybrid mice; studies with recombinant murine DNase and with dexamethasone. Clinical and Experimental Immunology (106), pp. 243-252, 1996.
Malickova, Karin et al., Decreased Activity of DNase-I Predisposes to Immune-Mediated Complications IBD Patients During Anti-TNFA Treatment, Gastroenterology, Abstract 202, vol. 138 (5 Supplement 1), S-37, 2010.
Maurer, HR, Bromelain: biochemistry, pharmacology and medical use, Cell Mol. Life. Sci., vol. 58, pp. 1234-1245, 2001.
Mel'Nikov D, et al., Voprosy onkologicheskoi pomoschi na etape reformirovaniya zdravookhraneniya, Ekaterinburg, pp. 159-161, 1996 (Reference in Russian and English-language translation).
Merkus et al., DNase treatment for atelectasis in infants with severe respiratory syncytial virus bronchiolitis, Eur Respir J, vol. 18, pp. 734-737, 2001.
Moreira VG et al., Usefulness of cell-free plasma DNA, procalcitonin and C-reactive protein as markers of infection in febrile patients, Annals of Clinical Biochemistry, vol. 47, pp. 253-258, 2010.
Morton CO, et al., Dynamics of extracellular release of *Aspergillus fum iga tus* DNA and galactomannan during growth in blood and serum, J. Med. Microbiol., vol. 59, pp. 408-413, 2010.
Mosca et al., Cell-free DNA in the plasma of patients with systemic sclerosis, Clinical Rheumatology, vol. 28, pp. 1437-1440, 2009.
Mueller V. and Schmit J., Fungal biodiversity: what do we know? What can we predict? Biodivers Conserv, 16:1-5, 2007.
Mutirangura A., Serum/plasma viral DNA: mechanisms and diagnostic applications to nasopharyngeal an cervical carcinoma, Ann NY Acad Sci., vol. 945, pp. 59-67, 2001.
Nestle & Roberts, An extracellular nuclease from *Serratia marcescens*, J. Biol. Chem., vol. 244, pp. 5213-5218, 1969.
Ngan et al., Remarkable Application of Serum EBV EBER-1 in Monitoring Response of Nasopharyngeal Cancer Patients to Salvage Chemotherapy, Ann. NY Acad. Sci., vol. 945, pp. 73-79, 2001.
Nikolenko G. N., Sozdanie rekombinantnykh antitel 17 protiv virusa kleschevogo entsefalita i izuchenie ikh svoystv, Avtoreferat dissertatsii na soiskanie uchenoi stepeni kandidata biologicheskikh nauk (author's abstract of PhD thesis in biological sciences), Koltsovo, pp. 1-2, 19, 1999 (Reference in Russian and English-language translation).
Oliven et al., Orally and Rectally Administered Streptokinase, Pharmacology, vol. 22, pp. 135-138, 1981.
Osivac et al., Reorganizacija DNK i biologicheskoje starenije, Biohimija, vol. 62, pp. 1491-1502, 1997 (Reference in Russian and English-language translation).
Perel'Man Mi, et al., Molekuljarnaja medicina i lechenie tuberkuleza, Problemi tuberkuleza, No. 5, pp. 5-7, 2001 (Reference in Russian and English-language translation).
Pisetsky, D., Immune response to DNA in systemic lupus erythematosus, Isr. Med. Assoc. J., vol. 3, pp. 850-853, 2001.
Pressler T., Review of recombinant human deoxyribonuclease (rhDNase) in the management of patients with cystic fibrosis, Biologics: Targets & Therapy, vol. 2, pp. 611-617, 2008.
Prince, W.S., et al, Pharmacodynamics of recombinant human DNase I in serum, Clin Exp Immunol, vol. 113, pp. 289-296, 1998.
Pulmozyme® (dornase alfa) Inhalation Solution product leaflet, Genetech, Inc., 2005.
Rao KS and Shrivastaw KP, Studies on the synthesis and degradation of DNA in developing and old chick cerebellum, Journal of Neurochemistry, vol. 27, pp. 1205-1210, 1976.
Raz E. et al., Anti-DNA antibodies bind directly to renal antigens and induce kidney dysfunction in the isolated perfused rat kidney, J Immunol., vol. 142, pp. 3076-3082, 1989.
Robertson D. and Smith AJ, The microbiology of the acute dental abscess, J. Med. Microbiol., vol. 58, pp. 155-162, 2009.
Schapira, Anthony H. V., Mitochondrial disease, Lancet, vol. 368, pp. 70-82, 2006.
Schloss et al., Status of the microbial census, Microbial and Molecular Biology Reviews, vol. 68, pp. 686-691, 2004.
Sergeeva L. M., Kliniko-laboratonaya otsenka mukoliticheskogo effekta pulmozima u bolnykh mukovistsidozom, Ekaterinburg, 1999, PhD dissertation in medicine, p. 9, paragraphs 2-3; p. 12, paragraph 4; p. 13, paragraphs 1-2; p. 17, paragraph 4; p. 18, paragraph 1; p. 30, paragraphs 3-4; p. 31, paragraph 2 (Reference in Russian and English Translation).
Shak et al., Recombinant human DNAse I reduces the viscosity of cystic fibrosis sputum, Proc. Natl. Acad. Sci. USA, vol. 87, pp. 9188-9192, 1990.
Sherry et al., Presence and Significance of Desoxyribose Nucleoprotein in the Purulent Pleural Exudates of Patients, Proc, Soc. Exp. Biol. Med., pp. 179-184, 1948.
Shevchuk, N.A., Vremyarazresheniy Immunofluorescentniy Amhz na DNK i Issiedovanie Socierzhaniya DNK v Syvorotke Cheloveka, Voprosi Medicinskoi Khimii, No. 4, 2001 (Reference in Russian and English Translation).
Shimony et al., Cell free DNA detected by a novel method in acute ST-elevation myocardial infarction patients, Acute Cardiac Care, vol. 12, pp. 109-111, 2010.
SIGMA Product Information sheet for Deoxyribonuclease I from Bovine Pancreas.
Simpson G., et al., Successful treatment of empyema thoracis with human recombinant deoxyribonuclease, Thorax, vol. 58, pp. 365-366, 2003.
Sugihara et al., Deoxyribonuclease treatment prevents blood-borne lier metastasis of cutaneously transplanted tumour cells in mice, Br. J. Cancer (67), pp. 66-70, 1993.
Supplementary European Search Report for European Patent Appl. No. EP06843990, dated Nov. 23, 2009 and cf Form 1507.
Supplementary European Search Report for European Patent Appl. No. EP04748955, mailed May 19, 2009.
Supplementary European Search Report for European Patent Appl. No. EP04775224, mailed Oct. 28, 2009.
Supplementary European Search Report for European Patent Appl. No. EP05745412, dated Jul. 10, 2009.
Supplementary European Search Report for European Patent Appl. No. EP03796243, dated Jan. 12, 2010.
Tetz VV and Tetz GV, Effect of Extracellular DNA Destruction by DNase I on Characteristics of Forming Biofilms, DNA and Cell Biology, vol. 29, pp. 399-405, 2010.

(56) References Cited

OTHER PUBLICATIONS

Tetz, GV, et al., Effect of DNase and Antibiotics on Biofilm Characteristics, Antimicrobial Agents and Chemotherapy, vol. 53, pp. 1204-1209, 2009.

Tetz, GV, et al., Effect of nucleolytic, proteolytic, and lipolytic enzymes on transfer of antibiotic resistance genes in mixed bacterial communities, Universal Journal of Medicine and Dentistry, vol. 1, pp. 46-50, 2012.

Translation of International Preliminary Report on Patentability for PCT/RU2003/000304, dated Nov. 1, 2005.

Translation of International Preliminary Report on Patentability for PCT/RU2004/000260, mailed Jan. 14, 2006.

Translation of International Preliminary Report on Patentability for PCT/RU2004/000261, mailed Dec. 2, 2005.

Translation of International Preliminary Report on Patentability for PCT/RU2004/000262, mailed Apr. 12, 2006.

Translation of International Preliminary Report on Patentability for PCT/RU2005/000236, mailed Feb. 13, 2008.

Translation of International Preliminary Report on Patentability for PCT/RU2006/000642, dated Jul. 7, 2009.

Ulrich & Friend, Toxicogenomics and drug discovery: will new technologies help us produce better drugs? Nature, vol. 1, pp. 84-88, 2002.

Varidase product information from EPGOnline, accessed on Dec. 12, 2011.

Vonmoos, P.L. and Straub, P.W., Absorption and hematologic effect of streptokinase-streptodornase (varidase) after intracavital or oral administration, Schweiz Med Wochenschr, vol. 109, pp. 1538-1544, 1979, Abstract.

Whitchurch, et al., Extracellular DNA Required for Bacterial Biofilm Formation, Science, vol. 295, p. 1487, 2002.

Yastrebova N. E., Razrabotka i izuchenie diagnosticheskikh vozmozhnostei immunofermentnykh test-sistem na osnove antigennykh preparatov zolotistogo stafilokokka i DNK, Avtoreferat dissertatsii na soiskanie uchenoi stepeni kandidata meditsinskikh nauk (author's abstract of PhD thesis in medical sciences), M., pp. 17-18, 1988 (Reference in Russian and English-language translation).

Yasuda, Toshihiro et al., Activity Measurement for Deoxyribonucleases I and II with Picogram Sensitivity Based on DNA/SYBR Green I Fluorescence, Analytical Biochemistry, vol. 255, pp. 274-276, 1998.

Ye et al., Quantification of Circulating Cell-Free DNA in the Serum of Patients with Obstructive Sleep Apnea-Hypopnea Syndrome, Lung, vol. 188, pp. 469-474, 2010.

Zaman, et al., Direct amplification of Entamoeba histolytica DNA from amoebic liver abscess pus using polymerase chain reaction, Parasitol. Res., vol. 86, pp. 724-728, 2000.

Zaravinos et al., Levosimendan reduces plasma cell-free DNA levels in patients with ischemic cardiomyopathy, J. Thromb. Thrombolysis, vol. 31, pp. 180-187, 2011.

Zhong et al., Presence of mitochondrial tRNA(leu(UUR) A to G 3243 mutation in DNA extracted from serum and plasma of patients with type A 2 diabetes mellitus. J. Clin. Pathol., vol. 53, pp. 466-469, 2000.

Electrophoteric profile of extracellular blood DNA after DNase treatment:
Left column – 10 mkg/ml
Right column – 0.5 mkg/ml

METHOD FOR TREATING SYSTEMIC BACTERIAL, FUNGAL AND PROTOZOAN INFECTION

CROSS-REFERENCE TO RELATED APPLICATIONS

This application is a continuation of U.S. application Ser. No. 12/835,036, filed on Jul. 13, 2010, now U.S. Pat. No. 8,431,123, which is a Continuation-in-Part of U.S. application Ser. No. 10/564,609, filed on Jan. 12, 2006, now abandoned, which is a U.S. national phase application under 35 U.S.C. §371 of International Patent Application No. PCT/RU2004/000260, filed on Jul. 1, 2004 (published in Russian on Jan. 20, 2005 as WO 2005/004789), which claims priority of Russian Federation Patent Application No. RU2004108057, filed on Mar. 12, 2004, and International Patent Application No. PCT/RU2003/000304, filed on Jul. 14, 2003, all of which are incorporated by reference as if fully rewritten herein.

BACKGROUND OF THE INVENTION

1. Field of the Invention

The present invention relates generally to medical treatment of the diseases that are accompanied by quantitative and qualitative changes of blood extracellular DNA and, more particularly, to a treatment of systemic bacterial, fungal and protozoan infections.

2. Description of the Related Art

Opposite to local infection the systemic infection is accompanied by the presence of pathogenic microorganisms or their components in the blood or tissues and organs other than primary infected area. The systemic infection is life threatening condition frequently accompanied by systemic inflammatory response syndrome (SIRS). Currently the main approach to treatment of systemic bacterial, fungal and protozoan infections is based on antibacterial chemotherapy (see Merck Manual of Diagnosis and Therapy; 16th Edition).

The rapid development of drug resistant bacteria or fungi or protozoa as well as self-protection of bacteria and fungi from therapeutic agents by formation of biofilms are considered as the main barrier for effective antibacterial chemotherapy. (David Davies; Nature Reviews Drug Discovery 2, 114-122, February 2003). Accordingly, the development of new effective, non-toxic methods which might increase the efficacy of antibacterial therapy in the course of systemic infections is an extremely important task.

It is known in the art that DNA of pathogenic microorganism and host DNA, originating from leucocytes is involved in formation and maintaining of purulent masses and biofilms in course of local infection. DNase enzyme has been available in medical practice in the USA for physicians for 40 years, since its discovery in the middle of the 20$^{th}$ century. Ayvazian disclosed the use of parenterally administered pancreatic DNase for destruction of DNA polymer in purulent exudates of patients suffering from pulmonary abscess (J. H. Ayvazian et al., American Review of Tuberculosis and Pulmonary Diseases, 1957, Vol. 76, N1) aiding in the clearing of respiratory airways. Reports indicate that this product had some clinical efficacy, but not enough to justify its widespread use. Bovine pancreatic DNase has been sold under the tradename Dornavac (Merck), but this product was withdrawn from the market mainly due to efficacy concern. Since that DNase enzyme is used almost exclusively to treat purulent masses in cystic fibrosis by inhalation (Pulmozyme; Genentech) or for local wound cleaning from purulent masses (Streptodornase).

Circulating extracellular nucleic acids were discovered more than 60 years ago. However until now they were considered only as useful diagnostic (Moreira V. G. et al., Usefulness of cell-free plasma DNA, procalcitonin and C-reactive protein as markers of infection in febrile patients, Ann Clin Biochem 2010 May; 47(Pt 3): 253-8. Epub 2010 Apr. 26) and research tool (Gal S, Wainscoat J S., Detection and quantitation of circulating Plasmodium falciparum DNA by polymerase chain reaction, Methods Mol Biol. 2006; 336:155-62; C. O. Morton et al, Dynamics of extracellular release of *Aspergillus fumigatus* DNA and galactomannan during growth in blood and serum, J Med Microbiol 59 (2010), 408-413).

Circulating extracellular nucleic acids have never been considered as potential therapeutic target in systemic infection. Accordingly, no therapeutic method was developed which efficiently targets extracellular blood DNA in systemic bacterial, fungi or protozoan infection. Thus it makes impossible to take any technical solution as prototype.

As used in this application, the following terms are meant to have the following corresponding definitions.

Deoxyribonuclease (DNase), as used herein, is any enzyme that catalyzes the hydrolytic cleavage of phosphodiester linkages in the DNA backbone.

Extracellular blood DNA number average molecular weight, as used herein, refers to the number average molecular weight is a way of determining the molecular weight of a polymer. Extracellular blood DNA molecules, come in different sizes (chain lengths), so the average molecular weight will depend on the method of averaging. The number average molecular weight is the ordinary arithmetic mean or average of the molecular weights of the individual DNA macromolecules. It is determined by measuring the molecular weight of n polymer molecules, summing the weights, and dividing by n. The number average molecular weight of extracellular blood DNA can be determined by gel electrophoresis. The shift of extracellular blood DNA bands to low-MW areas reflects a decrease in the number average molecular weight and in fact reflects enzymatic cleavage of extracellular blood DNA.

SUMMARY OF THE INVENTION

The object of this invention is to develop high-performance and low-toxic method for treatment of systemic infections that are accompanied by quantitative and/or qualitative change of composition of blood plasma extracellular DNA and caused by bacteria, fungi and protozoa.

According to the invention this task is resolved by introducing a treatment agent into a circulating blood system of a patient diagnosed with systemic infection caused by bacteria, fungi or protozoa when said treatment agent destroys extracellular DNA in said blood of said patient and wherein said treatment agent used to destroy said extracellular DNA is a DNase enzyme: said agent must be administered in doses and regimens which are sufficient to decrease the number average molecular weight of circulating extracellular blood DNA in the blood of said patient; such decrease of number average molecular weight might be measured by gel electrophoresis of extracellular blood DNA fraction from the blood of said patient. In one of preferred embodiments the method according the invention can be effectively applied for treatment of urinary tract infections and in particular for treatment of cyst infection in autosomal dominant polycystic kidney disease (ADPKD). A DNase enzyme may be further applied in a dose and regime that results in a DNA hydrolytic activity measured in blood plasma that exceeds 1.5 Kunitz units per 1 ml of blood plasma for more than 12 hours within a period of 24 hours.

The present invention suggests that systemic infections caused by bacteria, fungi and protozoa can be treated by reducing circulating extracellular blood DNA levels.

Development of systemic bacterial and fungal and protozoan infection in humans is accompanied by quantitative and/or qualitative change of blood extracellular DNA (Moreira V. G. et al., Usefulness of cell-free plasma DNA, procalcitonin and C-reactive protein as markers of infection in febrile patients, Ann Clin Biochem 2010 May; 47(Pt 3): 253-8. Epub. 2010 Apr. 26; Gal S, Wainscoat J S. Detection and quantitation of circulating Plasmodium falciparum DNA by polymerase chain reaction, Methods Mol Biol. 2006; 336: 155-62), There is no analysis of blood extracellular DNA spectrum and its biological role in systemic infection prior to this invention. A search of the prior art reveals no published data concerning an analysis of blood extracellular DNA spectrum in systemic infection performed by direct cloning and without use of polymerase chain reaction (PCR). PCR can pervert a pattern of blood extracellular DNA because of specificity of primers used for amplification. There is no available knowledge about genetic repertoire of extracellular blood DNA in patients suffering from said infections and about biological role of extracellular blood DNA in course of these diseases. Nothing is known about potential therapeutic value of extracellular blood DNA enzymatic destruction for treatment of systemic bacterial or fungal infections; so, taking into account all aforesaid, the invention complies with requirements of "novelty" criteria (N).

As the applicant established by direct cloning and sequencing of extracellular blood DNA without PCR (Polymerase Chain Reaction), the extracellular blood DNA of patients with systemic bacterial, fungal and protozoan infections contains the unique quantitative and qualitative repertoire of genes which non-randomly represents genome of microorganism causing the systemic infection and contains genetic elements required for maintaining and development of the disease. It was shown that extracellular blood DNA might promote the development of systemic infection, antibiotic resistance as well as biofilm formation by pathogenic microorganism.

It was established that enzymatic destruction of extracellular blood DNA by DNase enzyme when applied in certain surprisingly high specific doses has significant therapeutic effect on the course of systemic infections.

Aforesaid new characteristics of the claimed invention are based on new ideas about mechanism of development of systemic bacterial, fungal and protozoan infections. In this way the claimed method conformances to requirements of "invention step" criteria (IS).

BRIEF DESCRIPTION OF THE DRAWINGS

The advantages and features of the present invention have been explained by detailed description of embodiments with references to drawings.

DESCRIPTION OF THE PREFERRED EMBODIMENTS

Figure 1:
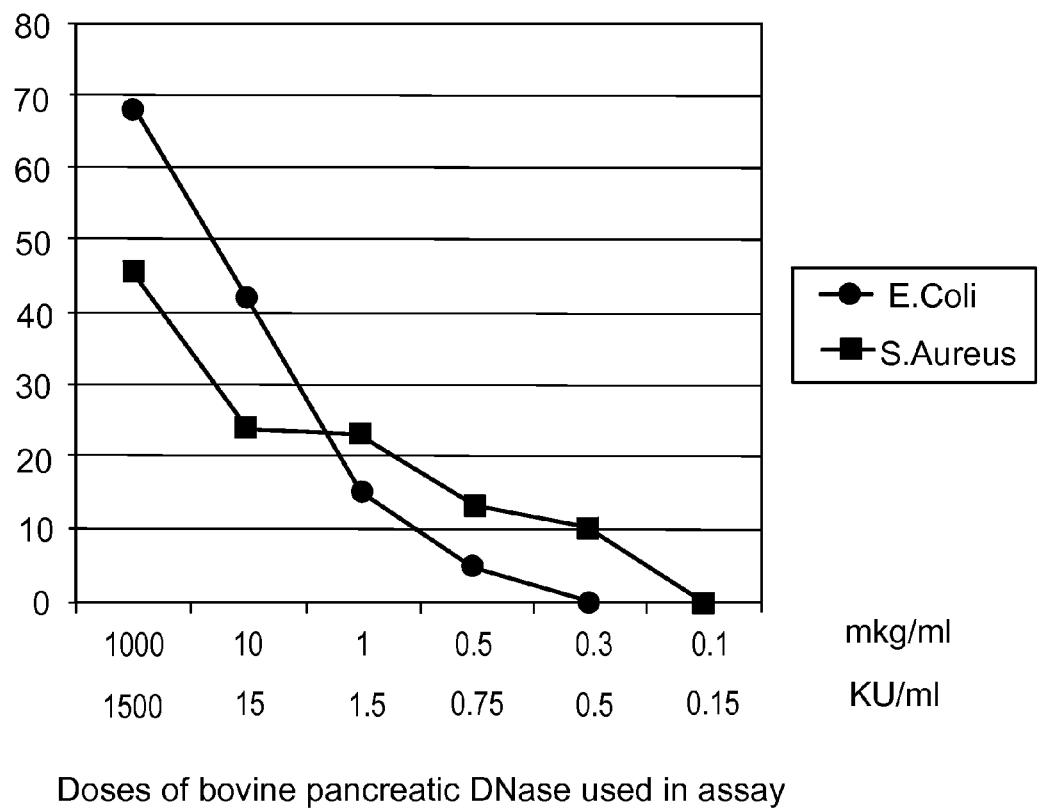
FIG. 1: Abrogation of pathogenic potential of circulating extracellular blood DNA by different doses of DNase. Doses of DNase less than 1 mkg/ml (1.5 Kunitz Units/ml) do not eliminate the pathogenic influence of extracellular blood DNA (promotion of biofilm growth) and cannot reduce the number average molecular weight of circulating extracellular blood DNA.
Figure 1:
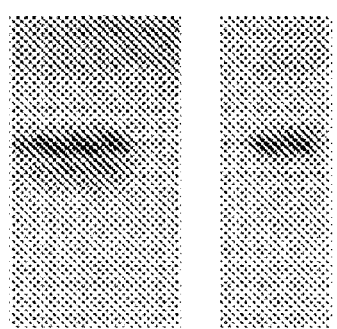

The inventive method is realized as follows:

Materials and Methods:

The following agents which destroy extracellular blood DNA were used: bovine pancreatic DNase (Sigma, specific activity 2400 Kunitz units/mg; Samson-Med, specific activity 1500 Kunitz units/mg), recombinant human DNASE 1 (Gentech, specific activity 1000 U/mg).

Extracellular DNA from blood plasma was isolated as follows: fresh plasma (no more than 3-4 hours after sampling) with anticoagulant (sodium citrate) was centrifuged on Ficoll-Plaque Plus (Amersham-Pharmacia) during 20 minutes at 1500 g. at room temperature. ½ of plasma was detached, not affecting the rest of cells on the Ficoll pillow, and further centrifuged at 10000 g. during 30 min for separation from cell fragments and debris. Supernatant was detached, without affecting of the sediment, and was topped up to 1% of sarkosil, 50 mM tris-HCl, pH 7, 6, 20 mM EDTA, 400 mM NaCl, and than mixed with equal volume of phenol-chloroform (1:1) mixture. The prepared emulsion was incubated during 2 hours at t=65° C., then phenol-chloroform mixture was separated by centrifuging (500 g during 20 minutes, room temperature). The procedure of deproteinization with phenol-chlorophorm mixture was repeated 3 times, and then the water phase was processed with chloroform and diethyl ether. Separation from organic solvents was made by centrifugation at 5000 g during 15 minutes. Then equal volume of izopropanol was added to resulting aqueous phase and the mixture was incubated overnight at 0° C. After sedimentation the nucleic acids were separated by centrifugation at 10000 g during 30 minutes. The sediment of nucleic acids was dissolved in of 10 mM tris-HCl buffer, pH 7, 6 with 5 mM EDTA, and inflicted to the CsCl gradient (1M, 2.5M, 5.7M) in test-tube for rotor SW60Ti. The volume of DNA solution was 2 ml, volume of each step of CsCl was 1 ml. Ultracentrifugation was conducted in L80-80 (Beckman) centrifuge during 3 hours at 250000 g. DNA was collected from the surface of each gradient step into fractions. These fractions were dialyzed during 12 hours (t=4° C.) and pooled. Presence of DNA in fractions was determined by agar electrophoresis and DNA was visualized by ethidium bromide staining. The amount of DNA was determined with spectrophotometer (Beckman DU70) in cuvet (100 mkl) at wavelength of 220-230 nm.

*Escherichia coli* K1, *Escherichia coli* ATCC 25922, *Staphylococcus aureus* VT38, *Staphylococcus aureus* VT-2003R, *Candida albicans* VT2002S, *P. berghei, A. fumigatus* VT2002A were used in this study. The strains designated VT were isolated from patients in the clinics of the St. Petersburg State Pavlov Medical University.

SHR and C57Bl mice were obtained from "Rappolovo" animal breeding house.

Example 1

Sequencing of Extracellular Blood DNA from the Patient Suffering from Bacillary Dysentery, Shigelosis Caused by *Shigella flexneri*

The probes of patient's extracellular blood DNA were taken before initiation of antibacterial chemotherapy and week after completion of the therapy. The extracellular DNA was cloned by the method which allows to get non amplified plasmid libraries of blood extracellular DNA with representativeness up to one million of clones with the average size of 300-500 base pairs. The DNA which has been isolated using the protocol specified above was treated with Proteinase K (Sigma) at 65° C. and subjected to additional phenol-chloroform extraction step with further overnight precipitation by ethanol. The DNA fraction was than treated by Eco RI restrictase or by Pfu polymerase (Stratagene) in presence of 300 mkM of all desoxynucleotidetriphosphates for sticky-ends elimination. The completed DNA was phosphorylated by polynucleotidkinase T4 and ligated to pBluescript plasmid (Stratagene), which had been digested with EcoRI or PvuII and dephosphorylated by phosphatase CIP (Fermentas). The process of ligation was conducted with Rapid Legation Kit (Roche). The ligated library was transformed into DH12S cells (Life Technologies) by electroporation (*E. coli* porator; BioRad). 12-20 electroporation covets were used for the transformation of one library. The library serial dilutions were cloned on 1.5% agar and LB media supplemented with ampicilline. In both cases the libraries represented 2-3×10$^6$ clones.

Analysis of 50 randomly selected clones with the size 300-1000 base pairs from the "before treatment" library revealed 12 clones containing *Shigella flexneri* DNA specified in the table below:

| Gene | Number of clones | Role in microorganism physiology |
|---|---|---|
| *S. flexneri* gcvP gene | 3 clones | Glycinedecarboxylase, P-protein of glycine cleavage system; known as the part of conserved metabolic pathways involved in the chronic persistence of microorganism in hosts. |
| *S. flexneri* yigM gene | 5 clones | Conserved membrane protein involved into biofilm formation |
| *S. flexneri* ubiB gene | 4 clones | Coding for ferrisiderophor reductase; ubiB *E. coli* mutants have alternate, as-yet unidentified hydroxylation mechanisms used in the anaerobic synthesis of ubiquinone. |

Analysis of 50 randomly selected clones with the size 300-1000 base pairs from the "after treatment" library does not revealed any DNA of bacterial origin.

Thus, extracellular blood DNA from patient having systemic bacterial infection contains significant non-random presence of pathogen-specific DNA coding for proteins involved in pathogen metabolic pathways and biofilm formation.

Example 2

Extracellular Blood DNA Promotes Pathogenic Behavior of Microorganism

The extracellular blood plasma DNA were obtained as follows: *S. aureus* VT38 and *Escherichia coli* K1 was injected intravenously at LD50 dose to 10 SHR mice (5 mice for each pathogen) to induce sepsis. On day 3 the diseased mice were sacrificed and extracellular blood DNA were collected as specified above.

Biofilm formation assay was performed as follows: *Escherichia coli* K1 and *Staphylococcus aureus* VT38 pathogenic strains were grown at 37° C., and liquid cultures were incubated without shaking. Before use in biofilm formation assay, cells were harvested and washed twice with 0.15M isotonic phosphate-buffered saline (pH7.2), and the cell suspensions were standardized to an optical density (OD) of 0.8 at 520 nm. The inoculums containing 7.53±0.22 log$_{10}$ CFU/mL, was added to the wells of 96-well plates (200 mkL/well) and plates were incubated for 24 hours at 37° C. Different amounts of extracellular blood plasma DNA were added to the wells 2 hours following seed.

Quantification of bacterial biomass in biofilms was performed by spectrophotometric method. Liquid medium with bacteria was aspirated from the wells, and the wells were then washed with isotonic phosphate buffer (0.15 M, pH 7.2) without disturbing the adherent film. Biofilm cells were scraped off the well walls and resuspended in 100 mL of phosphate buffer (0.15 M, pH 7.2). The well contents were then aspirated and bacteria were harvested by 10 min of centrifugation at 5000 rpm (Eppendorf 5415 C centrifuge; Eppendorf Geratgebau GmbH, Germany). The pelleted bacteria were diluted in 2 mL PBS, and absorption was determined at 570 nm in a LKB Biochrom Novaspec 4049 spectrophotometer (Cambridge, United Kingdom).

The results of experiment are presented in the tables below:

Effect of extracellular blood DNA derived from blood of *S. aureus* VT38 infected animals (EBDNA$_{VT38}$) on biomass of forming biofilm of *S. aureus* VT38 (OD at 570 nm)

| Control (PBS) | EBDNA$_{VT38}$ 0.5 mkg/well | EBDNA$_{VT38}$ 5 mkg/well | EBDNA$_{VT38}$ 50 mkg/well |
|---|---|---|---|
| 0.734 | 0.853 | 1.230 | 1.475 |

Effect of extracellular blood DNA derived from blood of *E. coli* K1 infected animals (EBDNA$_{K1}$) on biomass of forming biofilm of *E. coli* K1 (OD at 570 nm)

| Control (PBS) | EBDNA$_{K1}$ 0.5 mkg/well | EBDNA$_{K1}$ 5 mkg/well | EBDNA$_{K1}$ 50 mkg/well |
|---|---|---|---|
| 0.405 | 0.505 | 0.875 | 1.015 |

Thus, pathogen-specific extracellular blood DNA promotes the pathogen biofilm formation.

Example 3

Extracellular Blood DNA Promotes Spread of Antibiotic Resistance and Clonogenic Potential of Microorganisms The extracellular blood plasma DNA were obtained as follows: *Escherichia coli* K1 was injected intravenously at LD50 dose to 10 SHR mice to induce sepsis. On day 3 animals were treated with subtherapeutic doses of ampicillin and kanamycin for 3 consecutive days. On day 6 the diseased mice were sacrificed and extracellular blood DNA were collected as specified above. Biofilms of *E. coli* ATCC 25922 were grown as described in example 2 with or without extracellular blood DNA from *E. coli* K1 infected animals treated with antibiotics (50 mkg/well) on selection media containing ampicillin or kanamycin or both.

Colony-forming assay was performed as follows: The term "the number of CFU" means the number of viable bacteria that grow on nutrient media in the current conditions. Biofilms were grown in 96-well plates for 24 or 48 h. at 37° C. Liquid medium with bacteria was aspirated from the wells, which were then washed with isotonic phosphate buffer (0.15M, pH 7.2). Biofilms were scraped thoroughly, with particular attention to well edges. The well contents were aspirated again, then placed in 1.0 ml of isotonic phosphate buffer (0.15M, pH 7.2), and dispersed by drawing up and down through a fine-tip pipette, and the total CFU number was determined by serial dilution method and plating on appropriate media.

The results are presented at the table below:

| Antibiotic in selection media | Colony-forming Units per 1 ml | | | |
| --- | --- | --- | --- | --- |
| | Biofilms in EBDNA containing media | | Biofilms in regular media | |
| | 24 h. growth | 48 h. growth | 24 h. growth | 48 h. growth |
| Control | $3.0\text{-}5.0 \times 10^9$ | $6.0\text{-}8.0 \times 10^9$ | $1.0\text{-}3.0 \times 10^9$ | $2.0\text{-}4.0 \times 10^9$ |
| Km | $2.0\text{-}5.0 \times 10^9$ | $2.0\text{-}5.0 \times 10^9$ | $1.0\text{-}3.0 \times 10^9$ | $1.0\text{-}3.0 \times 10^9$ |
| Amp | $7.0\text{-}9.0 \times 10^8$ | $8.0\text{-}9.0 \times 10^8$ | $2.0\text{-}4.0 \times 10^8$ | $3.0\text{-}5.0 \times 10^8$ |
| Km + Amp | $1.0 \times 10^2\text{-}5.0 \times 10^3$ | $1.0 \times 10^2\text{-}5.0 \times 10^3$ | $0.0\text{-}1.0 \times 10^2$ | $0.0\text{-}10 \times 10^2$ |

Thus, pathogen-specific extracellular blood DNA promotes spread of antibiotic resistance and clonogenic potential of microorganism.

Example 4

Abrogation of Pathogenic Potential of Circulating Extracellular Blood DNA by Different Doses of DNase The extracellular blood plasma DNA were obtained as follows: *S. aureus* VT38 and *Escherichia coli* K1 was injected intravenously at LD50 dose to 10 SHR mice (5 mice for each pathogen) to induce sepsis. On day 3 the diseased mice were sacrificed and blood were collected into heparinized 1 ml tubes. 1 ml aliquots of blood from both *S. aureus* VT38 and *Escherichia coli* K1 infected animals were incubated for 30 min at 37° C. with different amounts of bovine pancreatic DNase, having specific activity of 1500 Kunitz units per milligram. After incubation the reaction was stopped by placing tubes on ice and extracellular blood DNA fraction was collected from each 1 ml sample as described in "Methods" section. The biofilm formation assay was performed as specified in Example 2 with presence of extracellular blood DNA extracted from blood samples incubated with DNase (extracellular DNA originating from 1 ml blood aliquot was assayed in 3 parallel wells). The electrophoresis assay of extracellular blood DNA was performed before and after DNase treatment. The results of experiment are presented in FIG. 1. Doses of DNase less than 1 mkg/ml (1.5 Kunitz Units/ml) do not eliminate the pathogenic influence of extracellular blood DNA (promotion of biofilm growth) and cannot reduce the number average molecular weight of circulating extracellular blood DNA.

Thus, unusually high doses of DNase required for realization of inventive treatment.

Example 5

Treatment of the Experimental Sepsis Caused by *Candida albicans* and *S. aureus*

Group 1-30 SHR mice were intravenously inoculated with $1 \times 10^{10}$ bacteria of pathogenic *S. aureus* VT-2003R strain. Recombinant human DNASE 1 (Genentech) was intraperitoneally administered at dose of 500 mkg/kg at 2, 6, 10 and 14 hours after the infection.

Group 2-10 SHR mice mice were intravenously inoculated with $1 \times 10^{10}$ bacteria of pathogenic *S. aureus* VT-2003R strain. Phosphate buffer was intraperitoneally administrated at 2, 6, 10 and 14 hours after the infection.

After the last injection of recombinant human DNASE 1, 20 mice from group 1 were divided into two subgroups (1a and 1b).

Subgroup 1a (10 mice) –2 hours following last injection of recombinant human DNASE 1 got intravenous injection of blood extracellular DNA isolated from blood plasma of not treated *S. aureus* VT-2003R infected animals at 15 hours post infection.

Subgroup 1b (10 mice) –2 hours following last injection of recombinant human DNASE 1 got intravenous injection of blood extracellular DNA isolated from blood plasma of not treated *C. albicans* VT2002S infected animals at 72 hours post infection.

The efficacies of DNase treatment and influence of extracellular blood DNA on disease course were assessed based on the survival rate during 32 hours after infection. The results of challenge experiments are presented at the table below The Survival Rate During Infection

| | 0 h. | 2 h. | 4 h. | 6 h. | 8 h. | 12 h. | 24 h. | 28 h. | 32 h. |
| --- | --- | --- | --- | --- | --- | --- | --- | --- | --- |
| Group 1 | 100% | 100% | 100% | 90% | 90% | 80% | 50% | 40% | 30% |
| Group 2 | 100% | 100% | 70% | 60% | 50% | 40% | 30% | 20% | 10% |
| 1a | — | — | — | — | — | — | 20% | 10% | 10% |
| 1B | — | — | — | — | — | — | 50% | 50% | 40% |

Group 3-10 SHR mice were intravenously inoculated with LD50 dose of pathogenic *C. albicans* VT2002S strain. Recombinant human DNASE 1 (Genentech) was intraperitoneally administered at 1 mg/kg dose twice daily on day 2, 3 and 4 after infection.

Group 4-10 SHR mice were intravenously inoculated with LD50 dose of pathogenic *C. albicans* VT2002S strain. Amphotericin B was intraperitoneally administered at 20 mg/kg dose twice a day on day 2, day 3 and day 4 after infection.

Group 5-10 SHR mice were intravenously inoculated with LD50 dose of pathogenic *C. albicans* VT2002S strain. Phosphate buffer was intraperitoneally administrated as negative control twice a day on day 2, day 3 and day 4 after infection.

The efficacies of treatments were assessed based on the survival rate during 7 days after infection. The results of challenge experiments are presented at the table below:

The Survival Rate During Infection

| Group | 1 day | 3 day | 5 day | 7 day |
|-------|-------|-------|-------|-------|
| 3 | 100% | 100% | 100% | 100% |
| 4 | 100% | 100% | 100% | 100% |
| 5 | 100% | 80% | 50% | 50% |

Thus the inventive method and is effective against systemic bacterial and fungal infection. Blood extracellular DNA from the infected animals possesses strong negative influence on the development of the infectious process.

Example 6

Treatment of Cerebral Malaria

Forty C57BI mice C57BI got intraperitoneal injection of erythrocytes, obtained from BALB/c mice previously infected with *P. berghei* ($10^6$ erythrocytes per mice). Mice were divided into 4 groups as follows:
Group 1-10 mice were treated with recombinant human DNASE 1 (Genentech) at 500 mkg/kg intramuscularly, 4 times per day, starting 24 h. following infection for three consecutive days.
Group 2-10 mice were treated with negative control (Phosphate buffer) at the same schedule.
Group 3-10 mice were treated with recombinant human DNASE 1 (Genentech) at 50 mkg/kg intramuscularly, 4 times per day, starting 24 h. following infection for three consecutive days The efficacies of treatments were assessed based on the survival rate during 7 days after infection. The results of challenge experiments are presented at the table below:

Viability of Mice on the 7th Day After Contamination

|  | Group 1 | Group 2 | Group 3 |
|---|---|---|---|
| Survival rate. % | 90 | 10 | 20 |

Thus the inventive method and is effective against systemic protozoan infection

Example 7

Treatment of Pulmonary Aspergillosis in Immunocompromized Mice

An isolate of *A. fumigatus* was obtained from the diagnostic microbiology laboratory at the St. Petersburg Medical Academy and cultured on Sabouraud dextrose agar at 25° C. for 3 days. 70 SHR mice were used in challenge experiments. Cyclophosphamide (Biochimic, Saransk) was administered intraperitoneally at 200 mg/kg of body weight 4 days prior to *A. fumigatus* challenge and 1 day after infection to induce a immunodeficient condition in mice. The PML counts were <100/µl for 6 days after infection. The inoculums, a 0.05-ml droplet containing $7.0 \times 10^5$ CFU/mouse, were given via intranasal route. The recombinant human DNASE 1 (Gentech) (at 5 mkg/kg, 50 mkg/kg, 100 mkg/kg, 500 mkg/kg, or 1000 mkg/kg) was administered intravenously twice daily for 4 days, starting at 1.5 h after infection. 2 mice from each group were sacrificed at day 5 to perform quantification of extracellular blood plasma DNA. The efficacies of DNase were assessed based on the survival rate at 10 days after infection. The results of challenge experiments are presented at the table below:

| DNase dose | Alive at day 10 | Extracellular blood plasma DNA concentration at day 5 |
|---|---|---|
| Negative control | 0(10) | 77 ng/ml; 111 ng/ml |
| 5 mkg/kg | 0(10) | 93 ng/ml; 85 ng/ml |
| 50 mkg/kg | 0(10) | 75 ng/ml; 115 ng/ml |
| 100 mkg/kg | 1(10) | 68 ng/ml; 70 ng/ml |
| 500 mkg/kg | 6(10) | 17 ng/ml; 15 ng/ml |
| 1000 mkg/kg | 8(10) | 12 ng/ml; 5 ng/ml |

Thus, high doses of DNase according to inventive treatment are able to decrease the quantities of circulating extracellular blood plasma DNA and are effective against systemic fungal infection Example 8

Pharmacodynamics of DNase Treatment

In order to explore pharmacodynamics and perform exposure-response analysis of action of DNase administered into a circulating blood system of a patient diagnosed with systemic infection on extracellular blood DNA we performed the clinical trial involving 25 patients suffering from odontogenic abscesses and phlegmons who had a 50% probability of disease progression despite initiation of treatment. (Scores between 91-159 points according to M. M. Solovev topical indicative prognosis scale).

The inclusion criteria were:
  Men and women 18 years or older
  Diagnosis proved by clinical, instrumental and laboratory assessment
  Admission at 5-6 days after manifestation of diseases
  Scores between 91-159 points according to M. M. Solovev topical indicative prognosis scale
The exclusion criteria were:
  Allergy for penicillins, cephalosporins or lincomycin
  Pregnancy or lactation
  Severe hepatic or renal diseases or underlying fatal illness
Surgical drainage was performed at admittance day (Day 1); Infusion therapy and antihistamine therapy were performed as supportive therapy. Antibacterial therapy comprises Cefazoline 1.0 g×3 times daily. Patients were randomly assigned into four groups to receive 50, 150, 300 and 600 mg daily doses of bovine pancreatic DNase (Samson Med). Daily dose of DNase were applied as 6 daily IM injections with 4 hours interval at Day 1, Day 2 and Day 3. The patients were sampled for electrophoresis analysis of extracellular blood DNA before first DNase injection and 24 h. later. At day 3 all patients were qualified by responsible physician either as "progressing" or "stable".

| Total number of patients | Daily Dose (mg) | Daily Dose (Kunitz Units) | Number of patients with decreased number average molecular weight of extracellular blood DNA. | Number of patients with disease progression |
|---|---|---|---|---|
| 9 | 50 | 85 000 | 0 | 5 |
| 8 | 150 | 255 000 | 0 | 3 |
| 8 | 300 | 510 000 | 5 | 1 |
| 8 | 600 | 1 020 000 | 8 | 0 |

Figure 2:
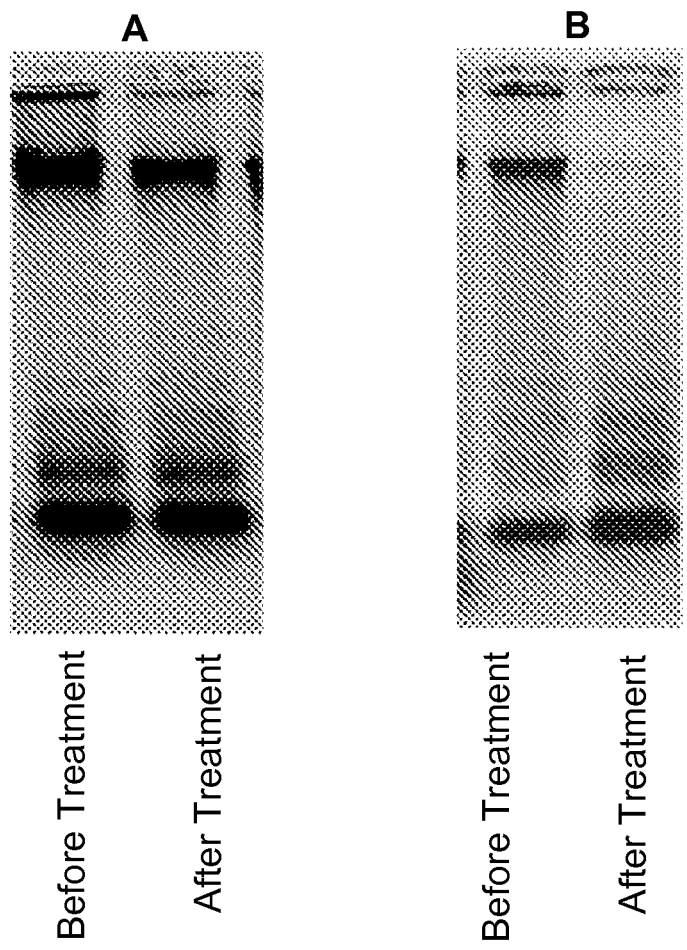
FIG. 2: Dynamics of number average molecular weight of extracellular blood DNA in progressing (A) and stable (B) patients: evident decrease of average molecular weight of extracellular blood plasma DNA (as measured by electrophoresis) in blood of stable patients while no dynamics in blood of progressing patients.

Thus, we surprisingly found that unusually high doses of DNase enzyme (almost ×10 times higher than those reported in the literature) required to achieve abrogation of disease progression and to achieve visible decrease of number average molecular weight of extracellular blood DNA (which in fact reflects enzymatic depolymerisation of DNA) (FIG. 2)

Example 9

Treatment of Urinary Tract Infection

Kidney filtration system works as natural "concentrator" for circulating extracellular blood DNA. Concentrated "transrenal DNA" further is excreted through lower urinary tract out from organism. Transrenal DNA is a extracellular urinary DNA that originates from circulating blood extracellular DNA. Transrenal DNA containing fetal sequences has been isolated from the urine of pregnant women, tumor-specific mutations have been detected in Transrenal DNA from patients with colon and pancreatic tumors, and donor DNA has been found in Transrenal DNA isolated from recipient urine. Furthermore, proviral HIV DNA, bacterial and parasite DNA sequences have been detected in Transrenal DNA from infected patients in very large quantities. (Umansky S R, Tomei L D, Expert Rev Mol Diagn. 2006 March; 6(2): 153-63. Transrenal DNA testing: progress and perspectives). In fact, that results in exposition of infective microorganisms spreading in kidneys and lower urinary tract to extremely large quantities of disease-stimulating extracellular blood DNA. Thus, systemic infection developing in kidneys and lower urinary tract might be especially sensitive to the treatment according present invention.

Autosomal dominant polycystic kidney disease (ADPKD) is a late-onset disorder characterized by progressive cyst development and bilaterally enlarged kidneys with multiple cysts. It is a genetic disorder resulting from mutations in either the PKD-1 or PKD-2 gene. Cyst formation begins in utero from any point along the nephron, although <5% of total nephrons are thought to be involved. As the cysts accumulate fluid, they enlarge, separate entirely from the nephron, compress the neighboring renal parenchyma, and progressively compromise renal function. Urinary tract infection occurs with increased frequency in ADPKD. Infection in a kidney or liver cyst is a particularly serious complication. It is most often due to Gram-negative bacteria and presents with pain, fever, and chills. Blood cultures are frequently positive, but urine culture may be negative because infected kidney cysts do not communicate directly with the collecting duct system.

A 43-year-old woman (height: 165 cm weight: 72 Kg), with established history of ADPKD, was admitted to Nephrology center of St. Petersburg Medical Academy with 25 day history of malaise, severe bilateral flank pain, dysuria, frequency, chills, and fever. On examination patient was febrile and ill. Pretibial edema and tenderness over the costovertebral angles were noted. Laboratory studies showed anemia, elevated level of blood urea nitrogen (BUN), serum creatinine, and serum glucose. Urinalysis showed pyuria, and urine culture yielded growth of Escherichia coli and Pseudomonas aeruginosa (more than $10^5$ colonies per high power field). Abdominal Ultrasonography demonstrated both enlarged kidneys measuring 20 cm on the right side and 23 cm on the left contained multiple cysts. The largest cysts in the right and left kidney were 7 cm and 12 cm respectively, with most of the remaining cysts measuring 3 to 5 cm. No hepatic cyst was noted. Intravenous piperacillin/tazobactam/ciprofloxacin therapy was initiated. Further ultrasonography investigation on the 7th day of treatment showed numerous cystic space-occupying lesions with low level internal echoes, and increased wall thickness of the cysts that representing infected cysts. Additional intravenous trimethoprim-sulfamethoxazole scheme was added to the assigned antibiotic therapy. This 2-week intensive antibacterial therapy had no beneficial effect and no ultrasonographic or symptomatic relief was achieved.

Figure 3:
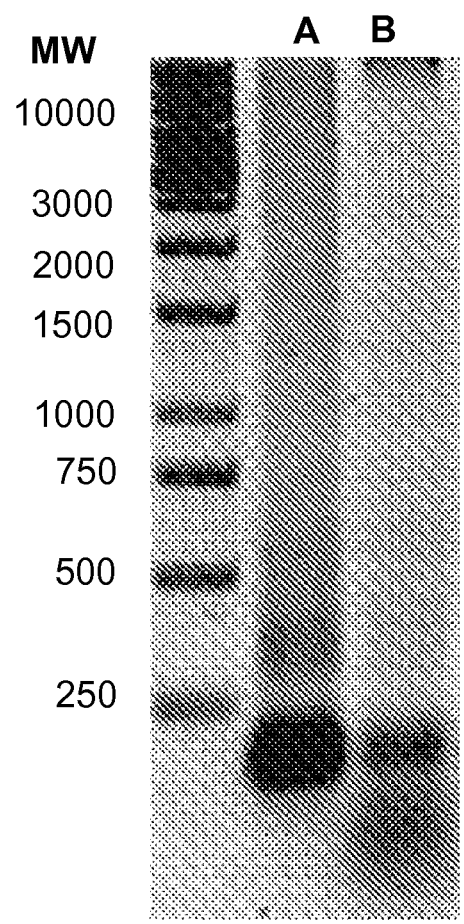
FIG. 3: Electrophoresis profile of circulating extracellular blood DNA from patient with autosomal dominant polycystic kidney disease (ADPKD) having infected cysts before (A) and 72 hours after initiation of DNase therapy (B). Significant decrease of number average molecular weight of circulating extracellular blood DNA may be noted.

After informing the patient and signed consent, the continuous intravenous infusion of bovine pancreatic DNase in daily dose of 1 000 mg (1 700 000 Kunitz Units) was initiated. After 3 days, fever disappeared and clinical state and laboratory tests showed improvement. Electrophoretic examination of circulating extracellular blood DNA showed significant decrease of number average molecular weight (FIG. 3). Repeated ultrasonography showed decreasing amount of internal echoes and thick septa of the drained cysts after one week of DNase therapy. Then, DNase infusion was stopped and antibiotic therapy was appropriately changed to oral trimethoprim-sulfamethoxazole. After 2 months of hospitalization, patient completely recovered and was discharged from clinics.

Example 10

Treatment of the Generalized Infection (Sepsis by *S. Pneumoniae*)

A 38-years-old man has been admitted to the Department of Internal Medicine of St. Petersburg Medical Academy in grave condition. Twelve days before he was diagnosed with acute respiratory viral infection. Because of febrile temperature, severe asthenia and chest pain he was further diagnosed with acute pneumonia 5 days prior to hospital admittance. Intramuscular cefazoline injection and oral roxitromycine were prescribed, but no improvement was noted. Two days before admittance to the hospital the patient has developed fever (39.5-40° C.), sickness, headache. Numerous hemorrhagic rush on the skin, muscle pain, jaundice and diarrhea appeared in the last day before hospitalization. On admittance the temperature was 39.3° C., arterial pressure was 100/60; tachycardia of 120 beats per minute, negative meningeal symptoms, cold and cyanotic limbs were present. Data of laboratory examination: moderate leucocytosis and left shift of haemogram (18% of young forms), appearance of neutrophils with toxic granulation, increased bilirubin, AST and ALT. Numerous small zones of heterogeneity were found at liver' ultrasound examination. The patient was diagnosed as having sepsis. Bacteriological control of blood was performed. Intravenous gentamycin/ampicillin/metronidazole/heparin therapy were initiated. Despite intensive antimicrobial polychemotherapy, hemasorbtion and plasma transfusion patient' condition has become worse. Vancomycin' infusions were prescribed as *S. pneumoniae* was isolated from the patient' blood. During next 48 hours despite of vancomycin's infusions condition of patient continued to become worse. Symptoms of multiple organ failure have appeared. Continuous intravenous infusions of bovine pancreatic DNase at 800 mg/day (1 600 000 Kunitz units) dose were initiated following consent from relatives. Symptoms of condition' stabilization has appeared twelve hours after initiation of DNase infusion: improvement of peripheral blood circulation and of systemic hemodynamic indexes, appearance of urination. DNase infusions continued during next 5 days. At that time patient laboratory indexes, hemodynamics, renal function become normal and patient was transferred on self-breathing.

INDUSTRIAL APPLICABILITY

For the realization the methods there were used well-known materials and equipment manufactured in plant conditions and according to aforesaid the invention conformances to requirements of "industrial applicability" criteria (IA).

What is claimed is:

1. A method for treating a systemic infection caused by bacteria or fungi in a patient in need thereof, wherein the systemic infection is associated with elevation of level of blood extracellular DNA in circulating blood, wherein said method comprises a step of introducing into the blood circulation system of said patient a DNase enzyme in a dose and regimen which is sufficient to decrease the average molecular weight of the blood extracellular DNA in the blood of said patient as measured by gel electrophoresis.

2. The method according to claim 1, wherein the DNase enzyme is administered in a dose and regimen that results in a DNase hydrolytic activity measured in blood plasma that exceeds 1.5 Kunitz units per 1 ml of blood plasma for more than 12 hours within a period of 24 hours.

* * * * *